United States Patent [19]

Jaeger

[11] 4,262,533

[45] Apr. 21, 1981

[54] HEATED LIQUID SAMPLER

[76] Inventor: Ben E. Jaeger, Rt. 2, Box 49, Plano, Ill. 60545

[21] Appl. No.: 35,601

[22] Filed: May 3, 1979

[51] Int. Cl.³ .............................................. G01N 1/14
[52] U.S. Cl. ................................................. 73/422 TC
[58] Field of Search .......... 73/422 TC, 421 B, 422 R, 73/421.5 A; 137/340

[56] References Cited

U.S. PATENT DOCUMENTS 2,865,394  12/1958  Presley ................................ 73/421 B

FOREIGN PATENT DOCUMENTS 747424   8/1970  Belgium .............................. 73/422 TC
1188836  3/1965  Fed. Rep. of Germany ...... 73/422 TC
2246672  7/1974  Fed. Rep. of Germany ...... 73/422 TC
491076   2/1976  U.S.S.R. ............................. 73/422 TC Primary Examiner—S. Clement Swisher
Attorney, Agent, or Firm—Gary, Juettner & Pyle

[57] ABSTRACT

A sampling apparatus for communicating with the interior of a vessel containing a liquid at an elevated temperature extracts a liquid sample of predetermined volumetric displacement from the vessel and maintains the sample at or above the elevated temperature or within a selected temperature range while conveying the same to a point of collection. If desired, an environment control medium may be maintained about the sample while within the sampler. In this manner, the sampler may advantageously be used to obtain samples of liquids which solidify, thicken, change in property and/or become unstable unless temperature controlled, or which must be maintained in a controlled environment during collection.

4 Claims, 4 Drawing Figures

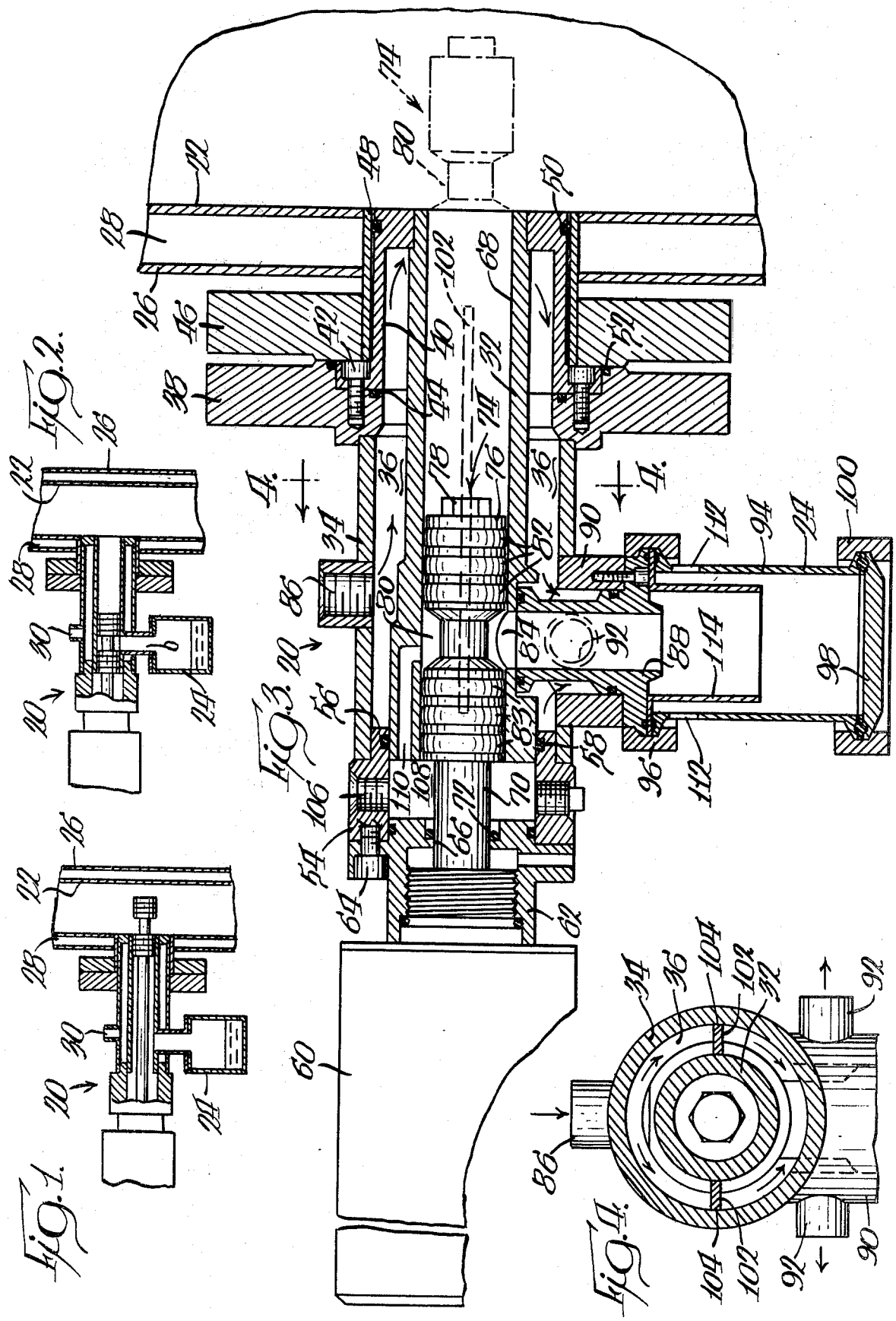

HEATED LIQUID SAMPLER

BACKGROUND OF THE INVENTION

The present invention relates to apparatus for extracting samples of liquid from flow lines or tanks thereof.

Various manufacturing operations require that the immediate or overall composition of a liquid flowing through a pipe or conduit be monitored or determined. Such monitoring ordinarily is accomplished with apparatus, often denoted as samplers, which take samples of liquid from the main body thereof. Where a composite sample of the liquid flow is required, the sampler is usually operated to withdraw a series of small, measured amounts of the liquid as it passes a sampling point. The individual samples are collected and represent a composite sample of the total volume of liquid.

Other uses for samplers are in on-line analysis applications in which the immediate composition of a liquid must be determined. For this application, the individual samples of liquid are not collected as a composite sample, but instead are separately analyzed.

To obtain the samples, some samplers continuously divert streams of liquid from the flow lines or tanks, and from the diverted streams the samples are removed in various ways. Attempts to withdraw small measured quantities directly from the pipes or tanks, however, have presented many problems not satisfactorily solved. For example, liquid receiving holes or slots in samplers adapted to be extended directly into a pipe require an orienting mechanism, and the sampled material often builds up in such holes and slots and either blocks the same or contaminates subsequent samples. In addition, conventional samplers are difficult to disassemble for inspection, cleaning and replacement of parts, and excessive leakage and clogging for the samplers are problems common to many types of samplers.

Heretofore samplers of the general type have been used to sample liquids which remain stable and in liquid form at room temperature. In recent years, however, a need has arisen to obtain samples of materials which are liquid at an elevated temperature, but which otherwise freeze, solidify, thicken, change in property and/or become unstable unless maintained at or above the elevated temperature or within a selected temperature range. Conventional samplers are usually exposed to and operated at ambient temperature. Consequently, such samplers cannot be used to obtain samples of such liquids since the sampler itself would cool the sample to a point whereat it would jam within or be extremely difficult to remove from the sampler, or perhaps to a point where it became unstable and exploded.

Another difficulty encountered with samplers of the conventional type is in maintaining the sample free from contamination from the time of its extraction and until it is delivered to a point of collection. With such samplers the extracted sample is usually exposed to atmosphere while in transit to the collection point, and for materials which absorb oxygen the composition of the sample may be altered so that an accurate analysis of the main body of liquid cannot be obtained.

OBJECTS OF THE INVENTION

An object of the present invention is to provide a sampler for withdrawing small measured quantities of samples directly from either a pipe or a tank and for maintaining the samples at or above a selected temperature or within a selected temperature range while transporting the same to a point of collection.

Another object of the invention is to provide such a sampler in which collected samples are protected from contamination during the sampling process.

A further object of the invention is to provide a sampler which cannot become clogged by material to be sampled, and which is excellently suited for automatic operation at selected intervals under control of a timing mechanism.

Yet another object of the invention is to provide such a sampler which is self-cleaning in its operation, which may readily be flushed with a solvent, and which is of simple and economical construction.

SUMMARY OF THE INVENTION

In accordance with the present invention, a sampling apparatus for obtaining samples of product from a product containing vessel, wherein the product is at a temperature other than ambient temperature, comprises a housing having a bore extending therethrough, wherein one end of said bore is for communication with the interior of the vessel, and a plunger in said bore and reciprocable therein. Said plunger has a recess intermediate its ends, and means are provided for reciprocating said plunger in said bore to project said recess from said one end of said bore and into the vessel to receive a sample of product therein and to then retract said recess from the vessel and to a point in said bore. Means are at said point in said bore for receiving the sample of product in said recess and means are included for maintaining a liquid seal between said one end of said bore and said point therein. In order to control the temperature of the sample during the sampling process, means are also provided for controlling the temperature of said housing to maintain the temperature of a product sample within a selected temperature range.

The invention also contemplates a method of obtaining samples of product from a product containing vessel, which includes the steps of extracting a discrete sample of the product from the vessel and transporting the sample to a point of collection, and controlling the temperature of the sample while transporting the same to the point of collection. In the case where the product in the vessel is at a temperature which is elevated with respect to ambient, said controlling step comprises exposing the sample to a heated environment while transporting the same to the point of collection. Should the product in the vessel be at a temperature which is lower than ambient, then said controlling step comprises exposing the sample to a refrigerated environment while transporting the same to the point of collection.

The foregoing and other objects, advantages and features of the invention will become apparent upon a consideration of the following detailed description, when taken in conjunction with the accompanying drawings.

BRIEF DESCRIPTION OF THE DRAWINGS

FIG. 1 is a schematic representation of a liquid sampler embodying the teachings of the present invention, showing a plunger of the sampler extended into a conduit for obtaining a measured sample of a liquid flowing therein;

FIG. 2 is similar to FIG. 1, and shows the plunger of the sampler withdraw from the conduit to a position whereat the sample is discharged into a container;

FIG. 3 is a side elevation view, partly in cross section, illustrating the structural details of a preferred embodiment of the sampler of the invention for obtaining a sample of fluid from a main body thereof and for maintaining the sample at or above a selected temperature or within a selected temperature range while transporting the same to a point of collection, and FIG. 4 is a cross section view taken substantially along the lines 4—4 of FIG. 3, and shows vanes within the sampler for distributing a heat transfer medium therein in a manner which causes uniform heating of the sampler.

DETAILED DESCRIPTION

Referring of FIGS. 1 and 2 there is shown a schematic representation of a sampler, indicated generally at 20, in accordance with the present invention. The sampler includes a plunger having an annular recess which is extendable into a conduit 22 for receiving a sample of a liquid flowing therein, and which is then retractable to exterior of the conduit for collection of the sample in a container 24. The recess is of a size to contain a precisely measured amount of the liquid, and the sampler may be cyclically actuated so that the material collected in the container represents a composite sample of material flowing through the conduit. The plunger may be actuated by a pneumatic or electric motor mounted on a rearward end of the sampler, and a plurality of seals on the plunger maintain a liquid seal between the interior of the conduit and the container, and between the container and the motor, during reciprocation of the plunger. In this manner, the sampler is generally insensitive to the pressure of the liquid in the conduit, and the collected sample is protected against contamination.

As may be appreciated, the annular recess which forms the sample chamber is washed clean by the liquid each time it is extended into the conduit, movement of the sample to the container is accomplished smoothly and without any slots or passages to clog, and there are no lines, diaphragms or pumps to impose internal shear or churning of the sample, whereby the samples collected in the container accurately represent the liquid in the conduit.

The sampler 20 is particularly adapted for extracting samples of liquid which are at an elevated temperature and which freeze, solidify, thicken, change in property and/or become unstable unless maintained at or above a selected temperature or within a selected temperature range. To this end, the conduit 22 is of the double wall type and includes an outer wall or jacketing 26 defining a circumferential passage 28 through which a heat transfer fluid flows in order to heat the conduit and maintain the liquid therein at an elevated temperature.

More specifically, as shown in FIG. 3 a sampler in accordance with the teachings of the present invention includes an inner tubular body or sleeve 32 coaxially within an outer cylindrical housing or jacket 34. The jacket forms a cylindrical chamber or passage 36 around the sleeve, and an annular sampler flange 38 connects with a forward end of the jacket. A cylindrical end housing 40 is joined and sealed with the flange by means of a plurality of fasteners 42 and a seal 44, and defines a forward extension of the chamber 36 to a point whereat a forward end of the housing extends radially inwardly to the sleeve 32 and closes the chamber. An annular product line flange 46 has an inner cylindrical sleeve 48 extending through the jacket 26 and passage 28 into communication with the interior of the product line conduit 22, and to connect the sampler with the product line the housing 40 is extended into the sleeve 48 to a point whereat the flanges 38 and 46 abut. A plurality of fasteners (not shown) secure the flanges together, and seals 50 and 52 form fluid tight connections between the housing 40 and sleeve 48 and between the flanges to prevent leakage of product from the conduit 22.

A head 54 is joined to a rearward end of the jacket 34, and an annular portion 56 of the head extends between the jacket and the sleeve 32 to close the rearward end of the chamber 36. A seal 58 forms a fluid tight connection between the head and the sleeve and a motor, which may comprise a pneumatic cylinder 60, has a forward adapter 62 connected to a rearward end of the head by means of a plurality of fasteners 64. The head has a bore 66 therein aligned with a passage or bore 68 through the sleeve, and cylinder rod 70 extends through the bores for reciprocation therein by a piston (not shown) of the pneumatic cylinder, with a seal 72 maintaining a fluid seal with the rod in the bore 66.

An elongated spindle or plunger assembly, indicated generally at 74, is at the forward end of the cylinder rod 70. The plunger assembly includes a spool 76 having an axial passage therethrough for reception of an elongate fastener or bolt 78 which is threaded into the forward end of the cylinder rod to secure the plunger assembly thereto. The spool is formed with a centrally located annular recess or sample chamber 80 of predetermined volumetric displacement, and separate sets 82 and 83 of three seals each are carried on the spool to opposite sides of the sample chamber. Actuation of the pneumatic cylinder thus reciprocates the plunger assembly within the sleeve 32, and the extent of travel is such that the assembly may be moved from an innermost position within the bore 68 whereat the sample chamber is aligned with a sample discharge port 84 in the sleeve, as shown in solid lines, to an outermost position whereat, as shown in phantom lines, a portion of the assembly including the sample chamber in position within the interior of the product line conduit 22.

The cylinder rod 70 is of a smaller diameter than the bore 66 in the head 54, and the spool 76 is of a smaller diameter than the bore 68 in the sleeve 32. In consequence, the annular seals 72, 82 and 83 themselves control the concentricity of the cylinder rod and plunger assembly within the bores, and function as bearings to enable the plunger assembly to reciprocate easily. This prevents direct sliding contact between the relatively "hard" components of the sampler, whereby the life of the sampler is extended and its repair frequency reduced.

It may be seen that the particular arrangement of the seals 82 and 83 at all times maintains a liquid seal between the sample discharge port 84 and the liquid in the conduit 22, yet enables discrete liquid samples to be conveyed to the discharge port. In particular, as the spindle assembly 74 moves rightward and partially out of the bore 68, the relative lengths of the spindle assembly and bore are such that the rearward seals 83 form a liquid seal with the bore forward of the sample discharge port before the forward seals 82 move out of the bore. Similarly, upon retraction of the spindle assembly into the bore the forward seals 82 reenter and form a liquid seal with the bore before the rearward seals 83 move across the discharge port. In consequence, a liquid seal is at all times maintained between the liquid in the conduit and the sample discharge port, and only the liquid sample collected in the sample chamber 80 ever reaches the discharge port.

It is to be appreciated that upon extending the spindle assembly to obtain a sample, the sample chamber 80 in the spool 76 is projected into the conduit 22 and exposed to the stream of liquid. Thus, the chamber is washed by the product stream upon each cycle of operation of the sampler. This minimizes a build-up of product in the sample chamber, as is typical in conventional samplers which use slots or holes for collecting a sample, since the open annular shape of the chamber and its direct exposure of the stream of product prevent it from becoming clogged by solids. It is therefore apparent that when the sample chamber is withdrawn from the conduit and into the bore it will carry a true sample of the liquid.

To the extent described, and except for the outer jacket 34, the sampler 20 is somewhat similar in structure and operation to samplers of the type disclosed in my U.S. Pat. No. 4,147,062, which issued Apr. 3, 1979. However, in improving upon such samplers, the sampler of the present invention may advantageously be used to obtain samples of liquid materials at elevated temperatures that would freeze, solidify, thicken, change in property and/or become unstable unless maintained at or above a selected temperature or within a selected temperature range. Obviously, if an attempt were made to collect such materials with a conventional sampler the same would be cooled by the sampler itself during the sampling process, resulting in jamming of the sampler, inaccuracy in the analysis of collected samples or, at worst, a severe instability and explosion of the sample within the sampler.

More particularly, the sampler of the invention has a novel structure which enables a sample of predetermined volumetric displacement to be collected from within the conduit 22 and to be maintained at or above a selected temperature or within a selected temperature range from its time of collection to its time of discharge through the port 84. To accomplish the foregoing, and with reference also to FIG. 4, the jacket 34 has an inlet 86 communicating with the cylindrical chamber 36 between the jacket and the sleeve 32, and a tubular neck 88 is sealed to and connected with the sleeve and a cylindrical radial extension 90 of the jacket with a passage through the neck in communication with the discharge port 84. A medial portion of the neck has an outer diameter which is smaller than the inner diameter of the radial extension 90, and forms with the extension a continuation of the chamber 36 to a pair of outlets 92 from the extension. The sample container 24 includes an outer cylindrical wall portion 94 connected with a lower end of the neck by means of a quick release clamp 96, and a bottom panel 98 is connected with the lower end of the wall by a quick release clamp 100. The clamps 96 and 100 permit either the entirety of the container to be removed from the sampler, or merely the bottom of the container to be opened, whereby to enable convenient retrieval of material samples collected therein.

As mentioned, product in the conduit 22 is maintained at an elevated temperature by a heat transfer medium flowing through the passage 28 between the outer jacket 26 and the conduit. To maintain an extracted product sample at the elevated temperature while it is transported from the conduit to the container 24, steam, water, anti-freeze, oil or any other suitable heat transfer medium at an elevated temperature is introduced into the inlet 86 to effect a flow of the heat transfer medium through the chamber 36 and around the sleeve 32 and the neck 88 to the outlets 92. In contacting the sleeve and the neck the heat transfer medium maintains the same at an elevated temperature, and the temperature of the heat transfer medium is selected so that sufficient heating of the sleeve and the neck occurs to maintain the temperature of the sample transported therethrough at substantially the same temperature as the product in the conduit. Thus, a product sample may be transported from the conduit to the collection container without experiencing a decrease in temperature, and should the nature of the product be such that it solidifies, thickens, changes its characteristics or becomes unstable upon experiencing a change in temperature, such product sample changes cannot occur within the sampler.

In order to uniformly distribute the heat transfer medium throughout the chamber 36 so that the sleeve 32 and neck 88 are evenly heated, a pair of deflector vanes 102 are positioned within the chamber. The vanes are generally planer, are attached to the sleeve along their length, and extend radially from the sleeve at positions 180° apart and at 90° spacings from the inlet 86. The vanes define relatively small openings 104 between their outer ends and the inner surface of the jacket 34, and extend lengthwise from positions close to the rearward end of the chamber at the head extension 56 to positions toward the forward end of the chamber. The vanes impede a relatively direct path for the heat transfer medium from the inlet 86 to the outlets 92, forcing the same to flow around the ends of the vanes and through the restricted openings 104 to ensure a uniform distribution of the heat transfer medium throughout the entirety of the chamber 36 and therefore around the sleeve and neck. To this end, it should be noted that the neck extends only a relatively short distance beyond the point whereat its outer surfaces are contacted by the heat transfer medium, which minimizes the unheated portion of the neck presented to the sample discharged into the container.

In addition to maintaining the temperature of a liquid sample at or above a selected temperature or within a selected temperature range, in accordance with another feature of the invention means are provided for controlling the environment of the sample as it is passed through the sampler and deposited in the container. In this respect, the head 54 has an inlet 106 in communication with a chamber 108 in the head. A passage 110 communicates between the chamber 108 and the bore 68 in the sleeve 32 opposite from the discharge port 84, and the arrangement is such that when the plunger assembly 74 is in its retracted position the sample chamber 80 lies intermediate the passage 110 and the discharge port 84. Thus, upon introduction of an environment control medium, such as an inert gas, through the inlet 106, the same surrounds the sample within the sample chamber 80 in the plunger assembly and travels with the sample through the neck 88 and into the container 24. To this end, the wall 94 of the container has a plurality of vents 112 formed therein for exit of the gas, and a shroud 114 extends downward from the neck to prevent any portion of the sample discharged into the container from being blown to exterior of the container through the vents 112. It is to be noted that the inner diameter of the shroud is relatively large compared with that of the passage through the neck, whereby the heated sample does not contact the shroud and is not cooled thereby.

A further advantage to the introduction of gas into the sampler to control the enivronment of the sample is that the flow of gas aids in moving the sample from the chamber 80 and through the neck 88 to the container 24. For particularly thick or viscous samples, a blast of gas may be applied to the inlet 106 to "wash" the sample into the container. Also, the arrangement facilitates cleaning of the sampler. Simply, a solvent may be introduced into the inlet 106 to flush the sample chamber and neck or, with the sampler disconnected from the product line, the plunger assembly may be reciprocated while solvent is introduced into the inlet to clean the entirety of the sampler.

The invention thus provides improved embodiments of liquid samplers which are particularly adapted to obtain samples of liquids at elevated temperatures, which liquids would otherwise solidify, thicken, become unstable and/or change their properties unless maintained during sampling at their elevated temperatures. In addition, provision has been made to control the environment of a collected sample, whereby the samples may be protected from exposure to external influences, such as oxygen in the atmosphere.

The sampler may readily be constructed of any suitable material, such as corrosion resistance metals or plastics, but preferably the components are all of the same material in order that they will have the same coefficient of thermal expansion in order to prevent dimensional operating variations in response to extremes of temperatures. Also, the sampler is excellently suited for automatic operation at selected intervals, for example under the control of a timing mechanism, and since the sample chamber extracts a predetermined and fixed volume of product with each cycle of operation of the sampler, when the samples are collected a composite sample is obtained that fully represents the process material composition. In addition, the jacket system operates as a containment housing for detecting leakage of sampled product that could occur if the inner sleeve 32 developed a crack, with the thermal transfer media at the outlets 92 simply being analyzed for the presence of product in order to detect the occurrence of such a leak.

Although the invention has been described in respect of maintaining product samples at an elevated temperature, it is also within the teachings and contemplation of the invention to maintain samples at temperatures below ambient. To this end, if the sampler is used to obtain samples of a refrigerated product, then a refrigerated heat transfer medium may simply be passed through the sampler. Obviously, if it is desired to raise or lower the temperature of a sample, rather than maintain it at the same temperature as the mass of product from which it was obtained, the temperature of the heat transfer media introduced into the sampler may be controlled accordingly.

While embodiments of the invention have been described in detail, various modifications and other embodiments thereof may be devised by one skilled in the art without departing from the spirit and the scope of the invention, as defined by the appended claims.

What is claimed is:

1. A sampling apparatus for obtaining samples of product from a product containing vessel wherein the product is at a temperature other than ambient temperature, comprising a housing having a bore extending therethrough, wherein one end of said bore is for communication with the interior of the vessel; a plunger having a recess intermediate its ends; means for reciprocating said plunger in said bore to project said recess from said one end of said bore and into the vessel to receive a sample of product therein and to then retract said recess from the vessel and to a point in said bore; means at said point in said bore for receiving the sample of product in said recess; means for maintaining a liquid seal between said one end of said bore and said point therein; and means for controlling the temperature of said housing to maintain the temperature of a product sampled within a selected temperature range, said means for controlling the temperature of said housing comprising jacket means around said housing forming a chamber between said jacket means and said housing, and means for introducing a heat transfer fluid at a selected temperature into said chamber in contact with said housing for controlling the temperature thereof, said jacket means having an inlet to said chamber for introduction of a heat transfer fluid into said chamber and an outlet from said chamber for exit of the heat transfer fluid, whereby heat transfer fluid may flow through said chamber to control the temperature of said housing, and including at least one fluid deflector in said chamber for controlling the flow of a heat transfer fluid therein to cause uniform contact of the heat transfer fluid with said housing.

2. A sampling apparatus for obtaining samples of product from a product containing vessel wherein the product is at a temperature other than ambient temperature, comprising a housing having a bore extending therethrough, wherein one end of said bore is for communication with the interior of the vessel; a plunger having a recess intermediate its ends; means for reciprocating said plunger in said bore to project said recess from said one end of said bore and into the vessel to receive a sample of product therein and to then retract said recess from the vessel and to a point in said bore; means at said point in said bore for receiving the sample of product in said recess; means for maintaining a liquid seal between said one end of said bore and said point therein; and means for controlling the temperature of said housing to maintain the temperature of a product sample within a selected temperature range, said means for controlling the temperature of said housing comprising jacket means around said housing forming a chamber between said jacket means and said housing, and means for introducing a heat transfer fluid at a selected temperature into said chamber in contact with said housing for controlling the temperature thereof, said jacket means having an inlet to said chamber for introduction of a heat transfer fluid into said chamber and an outlet from said chamber for exit of the heat transfer fluid, whereby heat transfer fluid may flow through said chamber to control the temperature of said housing, wherein said housing, said jacket means and said chamber are generally cylindrical, said inlet to and said outlet from said jacket means are positioned longitudinally therealong and generally on opposite sides thereof, and including a pair of fluid deflector vanes in said chamber for controlling a flow of a heat transfer fluid from said inlet, through said chamber and to said outlet, said deflector vanes being positioned to each side of said inlet, and wherein each said deflector vane extends longitudinally of said chamber toward, but not to, opposite longitudinal ends thereof, and radially of said chamber a distance less than the radial thickness of said chamber, whereby said deflector vanes restrict a circumferential flow of a heat transfer fluid through medial portions of said chamber and encourage a flow to opposite longitudinal ends thereof so that heat transfer fluid uniformly contacts said housing to uniformly control the temperature thereof.

3. A sampling apparatus for obtaining samples of product from a product containing vessel wherein the product is at a temperature other than ambient temperature, comprising a housing having a bore extending therethrough, wherein one end of said bore is for communication with the interior of the vessel; a plunger having a recess intermediate its ends; means for reciprocating said plunger in said bore to project said recess from said one end of said bore and into the vessel to receive a sample of product therein and to then retract said recess from the vessel and to a point in said bore; means at said point in said bore for receiving the sample of product in said recess; means for maintaining a liquid seal between said one end of said bore and said point therein; and means for controlling the temperature of said housing to maintain the temperature of a product sampled within a selected temperature range, said means for controlling the temperature of said housing comprising jacket means around said housing forming a chamber between said jacket means and said housing, and means for introducing a heat transfer fluid at a selected temperature into said chamber in contact with said housing for controlling the temperature thereof, said jacket means having an inlet to said chamber for introduction of a heat transfer fluid into said chamber and an outlet from said chamber for exit of the heat transfer fluid, whereby heat transfer fluid may flow through said chamber to control the temperature of said housing, and including at least one fluid deflector in said chamber for controlling the flow of a heat transfer fluid therein to cause uniform contact of the heat transfer fluid with said housing, wherein said jacket means inlet and outlet are positioned generally on opposite sides of said chamber, and said at least one fluid deflector comprises a pair of deflector vanes in said chamber to opposite sides of said inlet.

4. A sampling apparatus for obtaining discrete samples of product from a product containing vessel wherein the product is at a temperature other than ambient temperature, comprising a housing having a bore extending therethrough, wherein one of said bore is for communication with the interior of the vessel; a plunger having a recess intermediate its ends; means for reciprocating said plunger in said bore to project said recess from said one end of said bore and into the vessel to receive a sample of product therein and to then retract said recess from the vessel and to a point in said bore; means at said point in said bore for receiving the sample of product in said recess; means for maintaining a liquid seal between said one end of said bore and said point therein; and means for controlling the temperature of said housing to maintain the temperature of a product sample within a selected temperature range from the time the sample is extracted from the vessel and until it is received by said means at said point in said bore, said means for controlling the temperature of said housing comprising means for contacting the outer surfaces thereof from closely adjacent said one end of said bore to at least said point in said bore with a heat transfer medium at a selected temperature, wherein the heat transfer medium is separate and apart from the product in the vessel, said means for controlling the temperature of said housing comprising jacket means around said housing forming a chamber between said jacket means and said housing from closely adjacent said one end of said bore to at least said point in said bore, and means for introducing a heat transfer fluid at a selected temperature into said chamber in contact with said housing for controlling the temperature thereof, said jacket means having an inlet to said chamber for introduction of a heat transfer fluid into said chamber and an outlet from said chamber for exit of the heat transfer fluid, whereby heat transfer fluid may flow through said chamber to control the temperature of said housing, wherein said housing, said jacket means and said chamber are generally cylindrical, said inlet to and said outlet from said jacket means are positioned longitudinally therealong and generally on opposite sides thereof, and including a pair of fluid deflector vanes in said chamber for controlling a flow of a heat transfer fluid from said inlet, through said chamber and to said outlet, said deflector vanes being positioned to each side of said inlet.

* * * * *